(12) United States Patent
Joshi et al.

(10) Patent No.: US 10,433,807 B2
(45) Date of Patent: Oct. 8, 2019

(54) POWER SUPPLY COMPONENTS AND TECHNIQUES FOR HYBRID X-RAY SYSTEM

(71) Applicant: Dental Imaging Technologies Corporation, Hatfield, PA (US)

(72) Inventors: Sameer Anand Joshi, North Wales, PA (US); Bradley S. Carlson, Doylestown, PA (US)

(73) Assignee: DENTAL IMAGING TECHNOLOGIES CORPORATION, Hatfield, PA (US)

( * ) Notice: Subject to any disclaimer, the term of this patent is extended or adjusted under 35 U.S.C. 154(b) by 9 days.

(21) Appl. No.: 15/594,924

(22) Filed: May 15, 2017

(65) Prior Publication Data

US 2017/0245827 A1     Aug. 31, 2017

Related U.S. Application Data

(63) Continuation of application No. 14/811,576, filed on Jul. 28, 2015, now Pat. No. 9,649,078.

(51) Int. Cl.
*A61B 6/00* (2006.01)
*A61B 6/10* (2006.01)
*A61B 6/14* (2006.01)

(52) U.S. Cl.
CPC ............... *A61B 6/56* (2013.01); *A61B 6/107* (2013.01); *A61B 6/14* (2013.01); *A61B 6/40* (2013.01); *A61B 6/44* (2013.01); *A61B 6/4405* (2013.01); *A61B 6/4429* (2013.01); *A61B 6/586* (2013.01);

(Continued)

(58) Field of Classification Search
None
See application file for complete search history.

(56) References Cited

U.S. PATENT DOCUMENTS 5,781,610 A     7/1998  Miles
5,867,561 A *   2/1999  Strasser ............... A61B 6/4405
                                                      378/101

(Continued)

FOREIGN PATENT DOCUMENTS

GB     2370634 B     2/2005
WO     9723120 A1    6/1997

(Continued)

OTHER PUBLICATIONS

International Search Report and Written Opinion for Application No. PCT/US2016/044273 dated Sep. 20, 2016 (14 pages).

(Continued)

*Primary Examiner* — Hoon K Song
(74) *Attorney, Agent, or Firm* — Michael Best & Friedrich LLP

(57) ABSTRACT

A hybrid x-ray system that includes an x-ray device for mounted and portable use. The x-ray device includes a housing, an x-ray source coupled to the housing and configured to generate x-ray radiation, and a support connector coupled to the housing. The support connector is configured to mechanically couple to a support arm and to mechanically couple to a handle. The x-ray device include power circuitry or is otherwise configured to selectively receive power from a battery and an AC power source.

15 Claims, 13 Drawing Sheets

(52) U.S. Cl.
CPC ........... *A61B 6/4458* (2013.01); *A61B 6/4494* (2013.01); *A61B 6/54* (2013.01)

(56) References Cited

U.S. PATENT DOCUMENTS

| | | | | |
|---|---|---|---|---|
| 6,697,453 | B1* | 2/2004 | Mueller | G01N 23/207 |
| | | | | 378/198 |
| 6,965,118 | B2 | 11/2005 | Martin et al. | |
| 7,224,769 | B2 | 5/2007 | Turner | |
| 7,476,178 | B2* | 1/2009 | Tohta | B60W 10/06 |
| | | | | 477/107 |
| 7,496,178 | B2 | 2/2009 | Turner | |
| 2004/0218716 | A1* | 11/2004 | Freifeld | G01N 23/04 |
| | | | | 378/62 |
| 2011/0051902 | A1 | 3/2011 | Liu et al. | |
| 2013/0003923 | A1 | 1/2013 | Sackett | |
| 2013/0266122 | A1 | 10/2013 | Patil et al. | |
| 2014/0264061 | A1* | 9/2014 | Watanabe | A61B 6/4405 |
| | | | | 250/394 |
| 2015/0311738 | A1* | 10/2015 | Odaohhara | H02J 7/0063 |
| | | | | 320/128 |
| 2016/0033426 | A1 | 2/2016 | Georgeson et al. | |

FOREIGN PATENT DOCUMENTS

| | | |
|---|---|---|
| WO | 9944503 A1 | 9/1999 |
| WO | 2005081956 A2 | 9/2005 |

OTHER PUBLICATIONS

International Preliminary Report on Patentability for Application No. PCT/US2016/044273 dated Feb. 8, 2018 (5 pages).
Extended European Search Report from the European Patent Office for Application No. 16831293.2 dated Mar. 13, 2019 (6 pages).

* cited by examiner

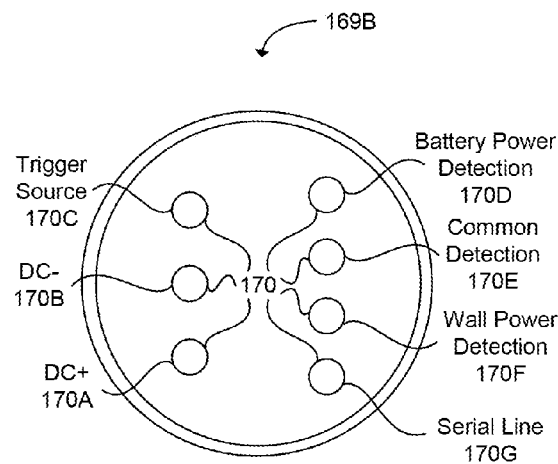
FIG. 8E
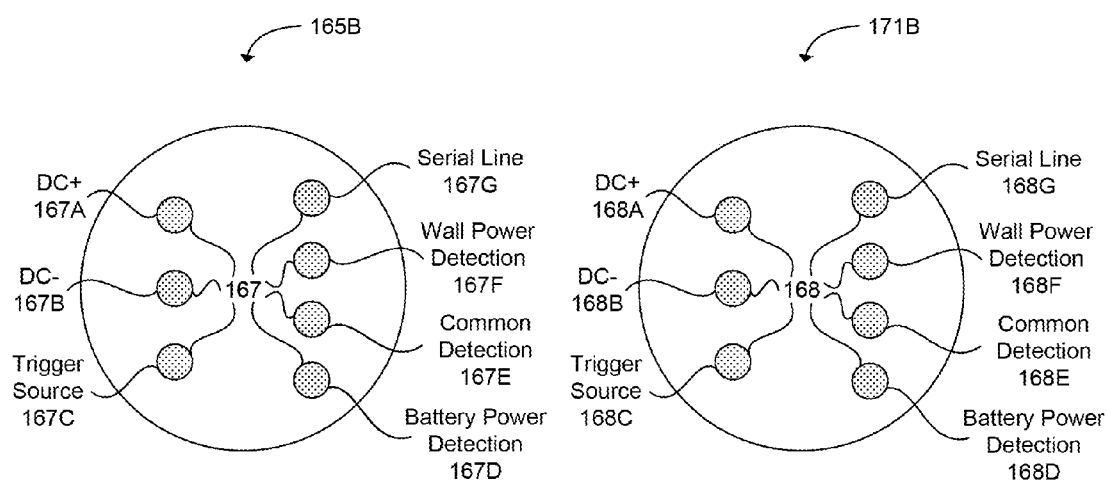
FIG. 8F
FIG. 8G

POWER SUPPLY COMPONENTS AND TECHNIQUES FOR HYBRID X-RAY SYSTEM

RELATED APPLICATIONS

This application claims priority to and is a continuation of U.S. application Ser. No. 14/811,576, filed on Jul. 28, 2015.

FIELD OF THE INVENTION

Embodiments of the invention relate to x-ray machines. More particularly, embodiments of the invention relate to a hybrid x-ray machine in which an x-ray source or device is detachably connected to a wall mount and configured to be used in at least one of two modes—a wall-mounted mode and a portable hand-held mode.

BACKGROUND

X-ray images are used in many medical and dental environments to show anatomy within a patient. For example, x-rays images are used in dentistry to image teeth and parts of the mouth. In general, the process involves generating x-rays and directing the x-rays at the patient's mouth. The x-rays are attenuated differently by different parts of the mouth (e.g., bone versus tissue) and this difference in attenuation is used to create an image by using an electronic image sensor, an phosphor imaging plate, film, or other type of receptor.

Although, x-rays are beneficial in the diagnoses of various diseases and ailments (e.g., broken bones or cavities), exposure to x-ray radiation can have harmful health effects. As a result, various processes, mechanisms, and materials can be used to reduce x-ray exposure to operators (e.g., dentists, and dental technicians) and patients, such as covering a patient's vital organs with a lead apron in dental offices during x-ray imaging. Due to the number of x-ray images taken by operators, extra precautions are implemented to reduce the operator's exposure to x-rays, such as standing behind a radiation shield (e.g., lead lined wall) when the x-rays are emitted from the x-ray device.

SUMMARY

In one embodiment, the invention provides a hybrid x-ray device that includes a housing, an x-ray source, a support connector, a shield connector, and an interlock. The x-ray source is coupled to the housing and configured to generate x-ray radiation. The support connector is coupled to the housing and configured to mechanically couple to a support arm. The shield connector is coupled to the housing and configured to mechanically couple to a removable radiation shield. The interlock is coupled to the x-ray source and configured to disable activation of the x-ray source when both: (a) the support connector is mechanically uncoupled from the support arm, and (b) the shield connector is mechanically uncoupled from the removable radiation shield.

In another embodiment, the invention provides a hybrid x-ray system for mounted and portable use that includes a removable radiation shield and a detachable x-ray device. The detachable x-ray device includes an x-ray source, a support connector, a shield connector, and an interlock. The x-ray source is configured to generate x-ray radiation. The support connector is configured to mechanically couple the detachable x-ray device to a handle or a support arm connected to a base. The support connector is also configured to provide power to the detachable x-ray device. The shield connector is configured to mechanically couple the detachable x-ray device to the removable radiation shield. The interlock is coupled to the x-ray source and configured to disable activation of the x-ray source when both: (a) the support connector is uncoupled from the support arm, and (b) the shield connector is uncoupled from the removable radiation shield.

In another embodiment, the invention provides a hybrid x-ray device configured to control the generation of x-ray radiation from an x-ray source of the hybrid x-ray device. The hybrid x-ray device determines when a support connector coupled to a housing of the hybrid x-ray device is mechanically coupled to a support arm supporting the hybrid x-ray device. The hybrid x-ray device also determines when a shield connector coupled to the housing of the hybrid x-ray device is mechanically coupled to a removable radiation shield. Then, the hybrid x-ray device disables the x-ray source when both (a) the support connector is uncoupled from the support arm, and (b) the shield connector is uncoupled from the removable radiation shield.

Other aspects of the invention will become apparent by consideration of the detailed description and accompanying drawings.

BRIEF DESCRIPTION OF THE DRAWINGS

FIGS. 8B-8G are views of connectors for an x-ray tube head, an extension arm, and a handle of the hybrid x-ray system, shown in FIGS. 3 and 8A, illustrating electrical contacts of the connectors.

DETAILED DESCRIPTION

Figure 1:
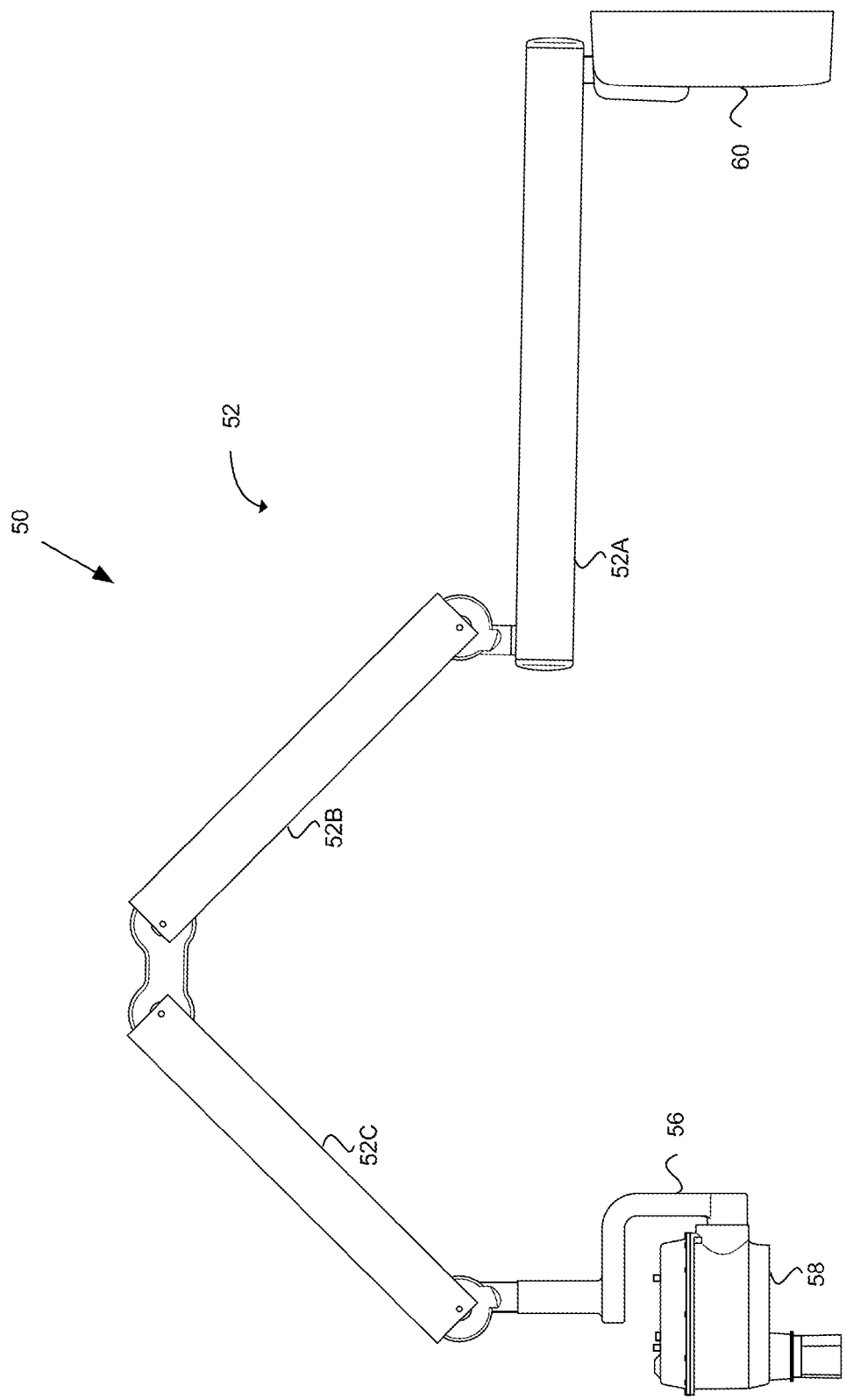
FIG. 1 is a side view of an x-ray device mounted to a support arm.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. The same reference numerals in different drawings represent the same element. Numbers provided in flow charts and processes are provided for clarity in illustrating steps and operations and do not necessarily indicate a particular order or sequence.

FIG. 1 illustrates a fixed x-ray system 50. The system 50 is designed for permanent installation in an examination or similar room of a dental office or similar facility. The system 50 includes an extension arm 52 having multiple links 52A, 52B, and 52C. At one end of link 52C is a support arm 56. An x-ray device 58 used in dental imaging is fixed to the support arm 56. The extension arm 52 is mounted to a wall or other support surface via a base 60. The links 52A, 52B, and 52C of the extension arm can be manipulated in order to position the x-ray device 58 at a desired location during image capture. The x-ray device 58 includes an x-ray source (not shown) that emits x-rays towards a specified anatomical area of interest or target area. A portion of the x-rays reflect off the target area as backscatter x-rays. Backscatter includes the radiation that reflects from the target area and any other objects that might receive radiation from the device 58 (e.g., the patient and surrounding objects). To reduce the operator's exposure to general x-ray radiation and backscatter, the operator can move into an adjacent room or behind a radiation shield during the imaging procedure. In some configurations, controls used to trigger the x-ray device 58 are located behind a radiation shield or the adjacent room to ensure that the operator is protected during x-ray imaging.

Figure 2:
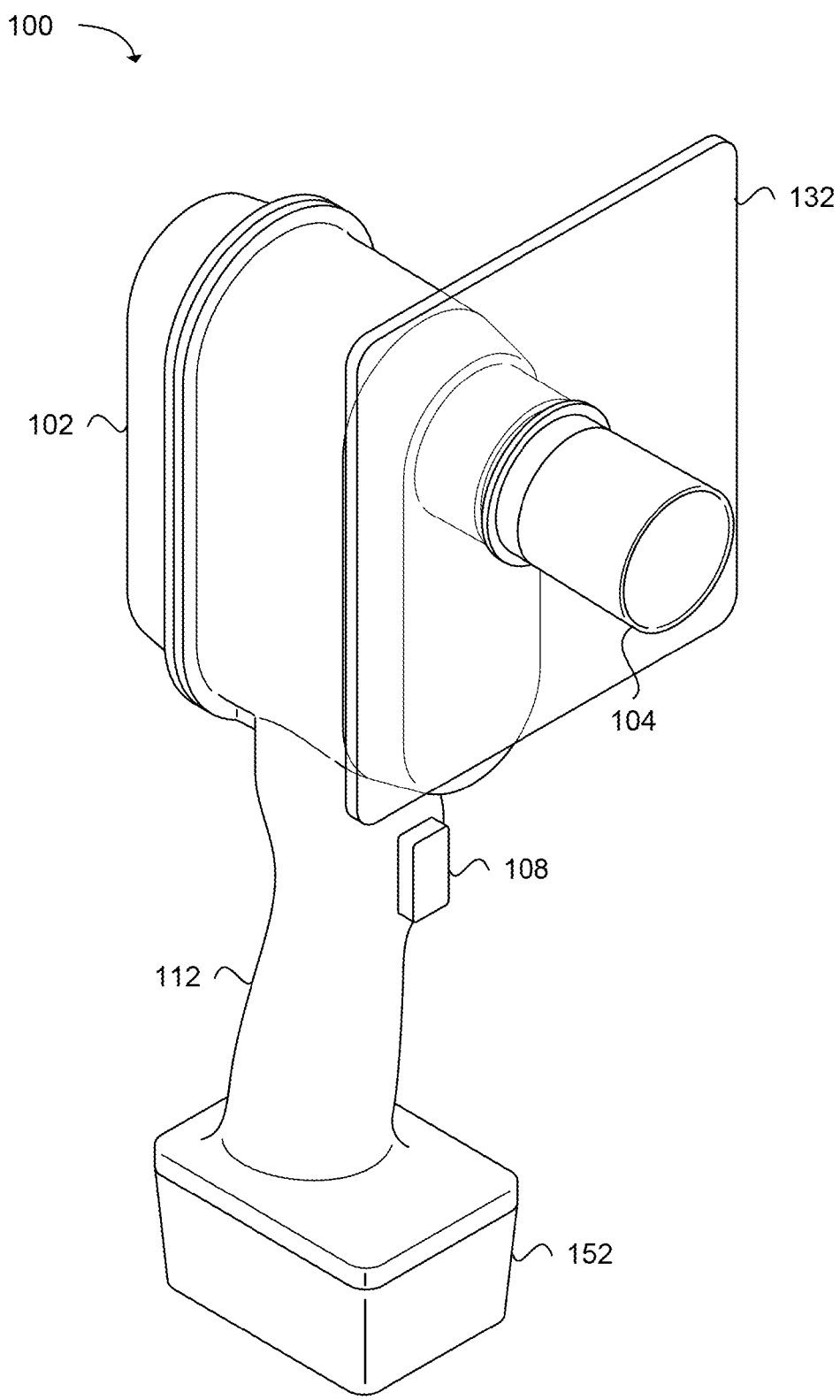
FIG. 2 is a perspective view of a portable x-ray system configured to operate using battery power and having a radiation shield.

FIG. 2 illustrates a portable x-ray device 100 (e.g., a hand-held device) that can also be used in dental imaging. The device 100 includes an x-ray generator or source 102, a collimator cone 104, a trigger 108, and a handle 112. Because the operator is holding the portable x-ray device 100 and can be exposed to backscatter, the device 100 includes features designed to reduce the amount of backscatter to which the operator is exposed. The device 100 includes a radiation shield 132 designed to at least partially shield the user from x-ray backscatter. The radiation shield 132 is permanently fixed in place or otherwise attached so that it cannot be readily removed.

The portable x-ray device 100 (FIG. 2) has certain advantages relative to the fixed x-ray system 50 (FIG. 1). For example, because the radiation shield 132 protects the operator from backscattered radiation, the operator can stay with a patient during the imaging procedure (i.e., the operator does need to leave the room during x-ray imaging). As a result, an x-ray image or radiograph can be taken any time during the evaluation or treatment of the patient, which can be particularly helpful with sedated patients, children, elderly patients, or special-needs patients where the operator's physical presence may be needed to, for example, physically position or hold the patient or to reassure the patient. In addition, because the portable x-ray device 100 is not constrained to a particular location, the portable x-ray device 100 can be moved to various treatment rooms in a dental office or facility. As a consequence, it may be unnecessary to permanently install x-ray systems in multiple rooms of the facility and the overall number of x-ray devices needed may be reduced. A corresponding decrease in equipment expenses may also be realized.

While portable x-ray devices 100 have certain advantages, they also have some disadvantages. For example, the portable x-ray device 100 is typically powered by a battery, a battery pack, or other electrical storage device. Generating x-ray radiation typically requires a relatively large amount of energy. As a consequence, the batteries used in portable x-ray devices 100 are often relatively large, which can make the portable x-ray device 100 relatively heavy and difficult to manipulate. In addition, portable x-ray devices 100 may have limited voltage and current settings for x-ray exposure due to the relatively limited power available from their batteries. Of course, batteries must also be periodically charged. In the illustrated example, the device 100 includes a battery 152 that provides direct current (DC) power. Batteries suitable for use in the device 100 include lithium-ion batteries.

On the other hand, a conventional wall (or ceiling) mount x-ray device or unit (for example, the system 50 in FIG. 1) typically uses grid power or power generated on the site of the dental facility. Such power is typically provided as alternating current (AC) power. In addition, such power is typically more than sufficient to provide adequate voltage and current for generating x-ray radiation at desired levels. Thus, fixed x-ray devices do not have the same limitations as portable x-ray devices 100 with respect to power or charging. In addition, since a fixed system 50 physically supports the x-ray source and provides for remote triggering, a fixed system does not have drawbacks associated with weight or backscatter radiation shields.

An x-ray source or device can be used in connection with an extension arm but also detached from the extension arm for portable use (e.g., hand-held operation), which combines the advantages of both a fixed x-ray device and portable x-ray device. An x-ray device and/or system that can be configured for portable use using, for example, battery power and configured to be coupled to support arms in a fixed system using, for example, wall power is referred herein as a hybrid x-ray device and/or system. Wall power can include AC power from the grid or DC power that comes from an AC to DC (AC/DC) converter.

Figure 3:
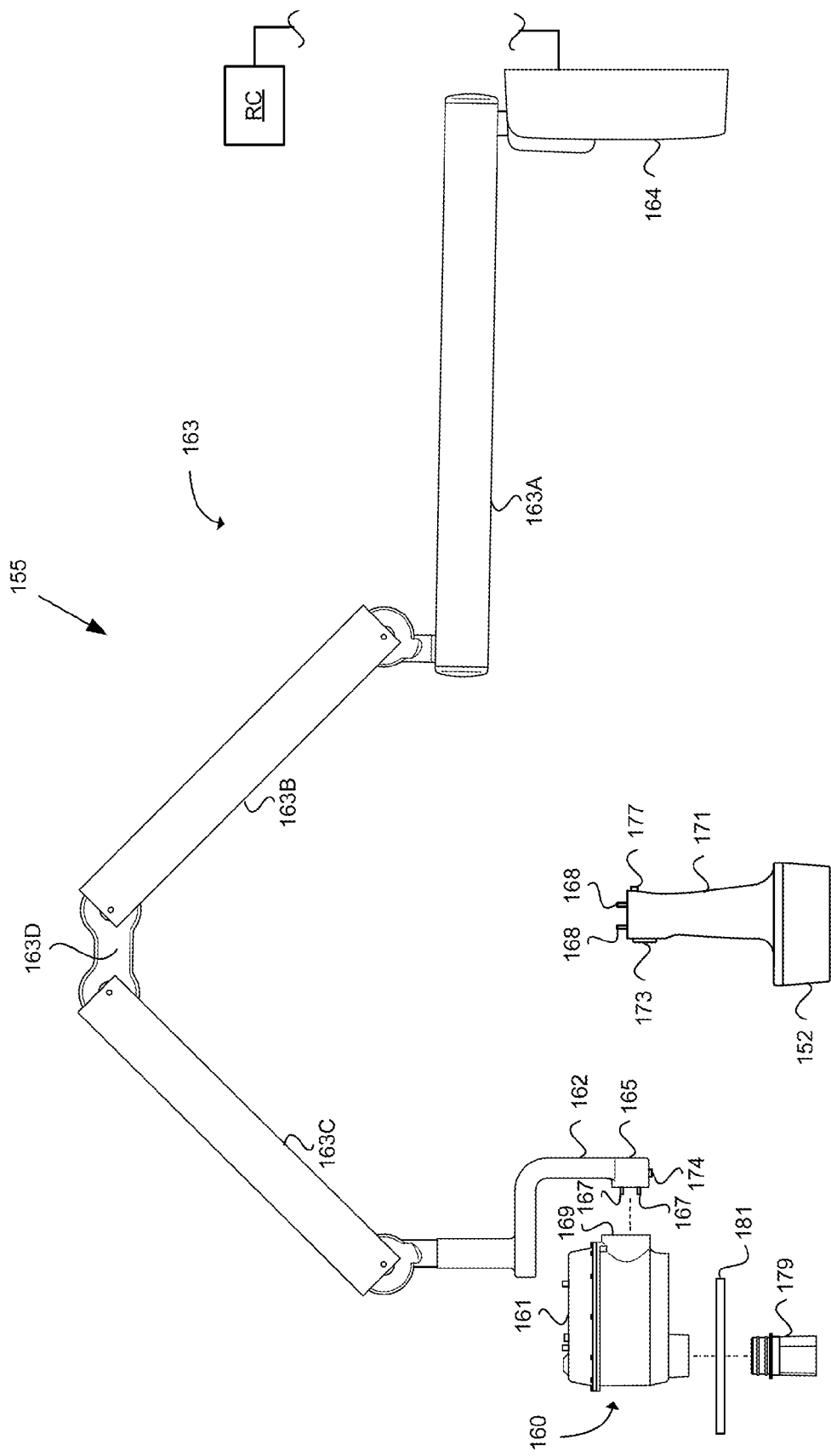
FIG. 3 is a side view of a hybrid x-ray system illustrating how the x-ray tube head may be connected to a support arm or a handle via coupling points.

FIG. 3 illustrates a hybrid x-ray system 155 having a removable or detachable x-ray device or x-ray tube head 160 (which is, more broadly, a hybrid x-ray device). The x-ray tube head 160 includes a housing 161 and can be detached from a support arm 162. The support arm 162 is attached to an articulating extension arm 163. The extension arm 163 includes links 163A, 163B, and 163C. Link 163C is connected to a wall-mounted base 164. The extension are may also include a brake 163D at a pivot point between links 163B and 163C.

The linked, extension arm 163 allows the operator to adjust positioning of the x-ray tube head 160 at a desired location. The extension arm 163 and support arm 162 can include power, control, and/or data cabling that connects the x-ray tube head 160 to a remote switch, control, and/or power source, schematically illustrated as a remote control (RC). These controls and connections may be made and provided through the base 164. The support arm 162 includes a plug end 165, with electrical pins or contacts 167 that are received by a socket 169 (i.e., power connector and/or control connector) or similar connector of the x-ray tube head 160. Although a particular configuration of pins and sockets are shown, it should be understood that various configurations of male and female connectors could be used. The socket 169 may be referred to as a support connector as it functions to assist in the connection of the x-ray tube head 160 to the support arm 162 and, ultimately, the articulating extension arm 163.

The x-ray tube head 160 may also be connected to a handle 171 having a trigger 173, a handle release 177, pins or contacts 168, and a battery 152 in a portable configuration.

The plug end 165 can include a support arm release 174 to detach the x-ray tube head 160 from the support arm 162. Similarly, the handle 171 can include the handle release 177 to detach the x-ray tube head 160 from the handle 171. Alternatively, the x-ray tube head 160 can include a release (not shown) to detach the x-ray tube head 160 from the support arm 162 or the handle 171.

A collimator cone 179 may be attached to the x-ray tube head 160. A removable or detachable radiation shield 181 may also be attached to the x-ray tube head 160.

When the x-ray tube head 160 is attached to the articulating extension arm 163, the x-ray tube head grid power and can provide the user a range of choices in the voltage (e.g., kV) and current (e.g., mA) settings that is similar to fixed x-ray systems 50 (FIG. 1). Of course, when detached from the articulating extension arm 163, the hybrid x-ray system 155 provides portability that is similar to that provided by a portable device 100 (FIG. 1).

The use of the hybrid x-ray system 155 can introduce some potential operator safety issues relative to x-ray exposure. As discussed previously in relation to FIG. 1, the operator of a typical wall mounted or fixed x-ray system 50 moves to a protected location (e.g., outside of the room in which imaging occurs during x-ray exposure to the patient). When using portable x-ray device 100 the operator is physically near the patient and can be exposed to backscatter radiation from various objects, such as the patient's teeth or fillings. When using the hybrid x-ray system 155 in a portable configuration or mode, similar backscatter radiation can occur. Thus, the hybrid x-ray system 155 preferably has a radiation shield 181 attached to it when used in a portable mode of operation. However, the radiation shield 181 is not needed when using the hybrid x-ray system 155 in a fixed or wall mount mode.

To comply with governmental safety regulations (e.g., U.S. FDA regulations), portable x-ray devices have a fixed or permanent radiation shield attached to the portable x-ray devices in order to shield the operator from backscatter. Because the radiation shield is mounted permanently, it is not possible to use the portable x-ray device without the protective radiation shield.

However, a permanent radiation shield is not useful in wall mount or fixed x-ray systems because in some situations, the radiation shield interferes with the patient or otherwise makes it difficult to position the x-ray source with respect to a digital sensor, film, or other receptor. For example, the radiation shield may prevent alignment of the x-ray device with a digital sensor or other receptor. Proper alignment is important to the quality of the resulting image. Misalignment can result in distortion and other defects. The radiation shield 181 can also potentially interfere with the apparatus used for holding the film or sensor (not shown) and/or an aiming ring on the x-ray device (not shown).

Embodiments of the invention disclosed herein help ensure adequate operator safety when using the hybrid x-ray system in a portable mode. For example, the x-ray source or x-ray tube head 160 of the hybrid x-ray system 155 can be configured (as described below) to only allow the x-ray tube head 160 to emit x-rays in one of two conditions: (1) when the radiation shield 181 is attached to the x-ray tube head 160, or (2) when the x-ray tube head 160 is docked to the support arm 162 and the hybrid x-ray device is operated in a fixed mount mode (e.g., via a wall or ceiling mount unit).

In the fixed mount mode an exposure can be initiated via a remote control (e.g., a switch or an actuator) remotely located from the x-ray tube head 160. The radiation shield 181 may or may not be attached onto the x-ray tube head 160 of the hybrid x-ray device when it is in a fixed or mount mode of operation.

Figure 4:
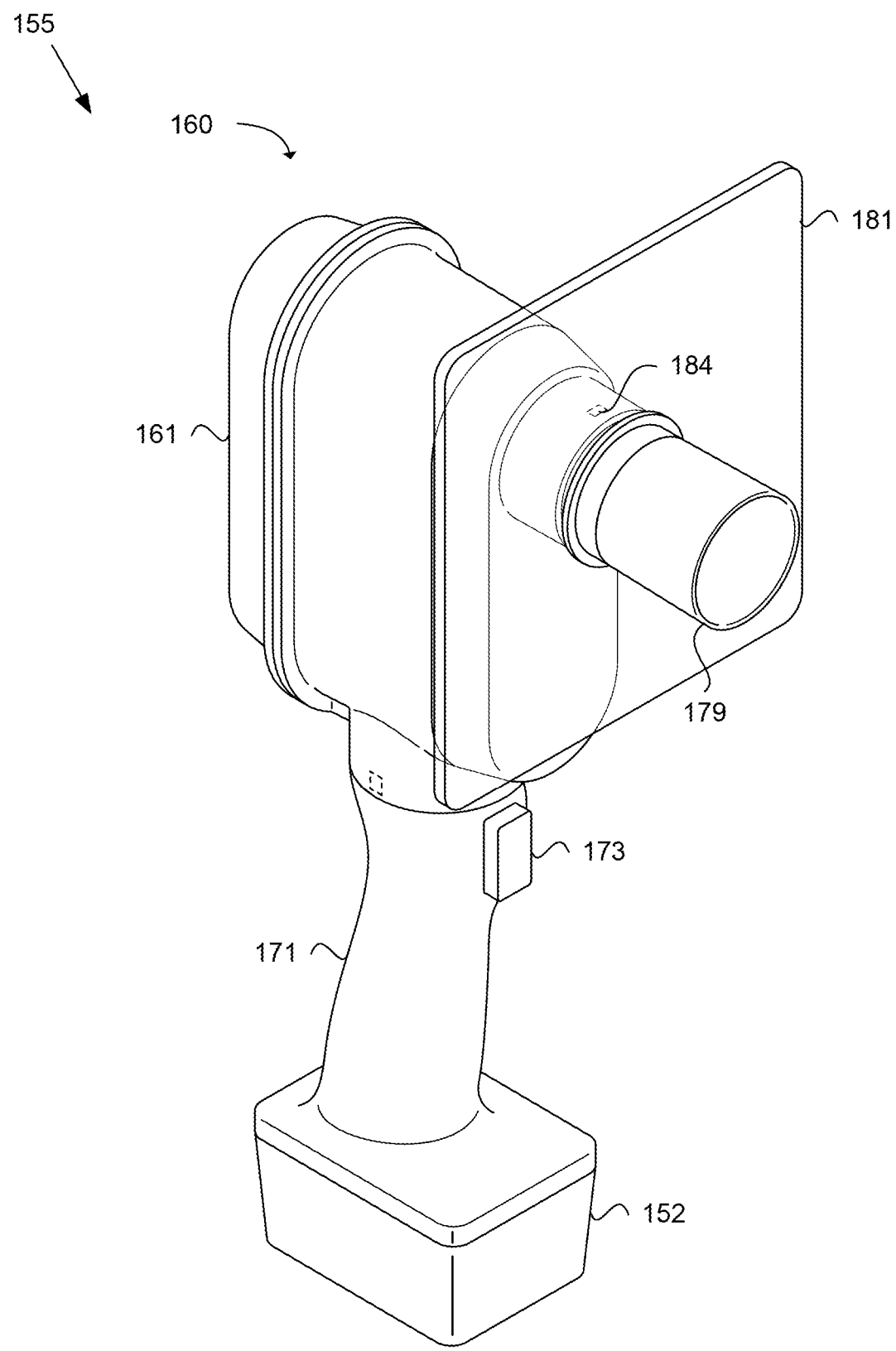
FIG. 4 is a perspective view of a hybrid x-ray system having a detachable radiation shield and configured to operate using battery power.

FIG. 4 illustrates one example of the hybrid x-ray system 155 in a portable configuration, where the x-ray tube head 160 is undocked from the support arm 162 and used as a portable x-ray unit. In the portable configuration, the hybrid x-ray system 155 and, more particularly, the x-ray tube head 160 is preferably enabled only when detachable radiation shield 181 is attached to the x-ray tube head 160. Different mechanisms can be used to ensure that the detachable radiation shield 181 is attached to the x-ray tube head 160 before the hybrid x-ray system 155 can be armed and used in an imaging procedure.

For example, the x-ray tube head 160 can include mechanisms to identify or detect the presence of the radiation shield 181 on the x-ray tube head 160 and/or a locked condition of the radiation shield on the x-ray tube head 160. Suitable identification or detection mechanisms include electro-mechanical devices (e.g., a physical switch, a sensor, and/or detector). Suitable identification devices also include electronic identification devices (e.g., radio-frequency identification (RFID) tags, automatic identification and data capture (AIDC) devices, and similar electronic devices). In the embodiment shown, a shield sensor 184 is used. Although a single sensor is shown in FIG. 4, multiple sensors or detectors in other configurations or combinations may also be used. The shield sensor 184 can include electrical contacts, optical features (e.g., infrared or light emitting diodes (LEDs and detectors)), magnetic features (e.g., Hall sensor), and/or other sensing technologies.

Figure 5A:
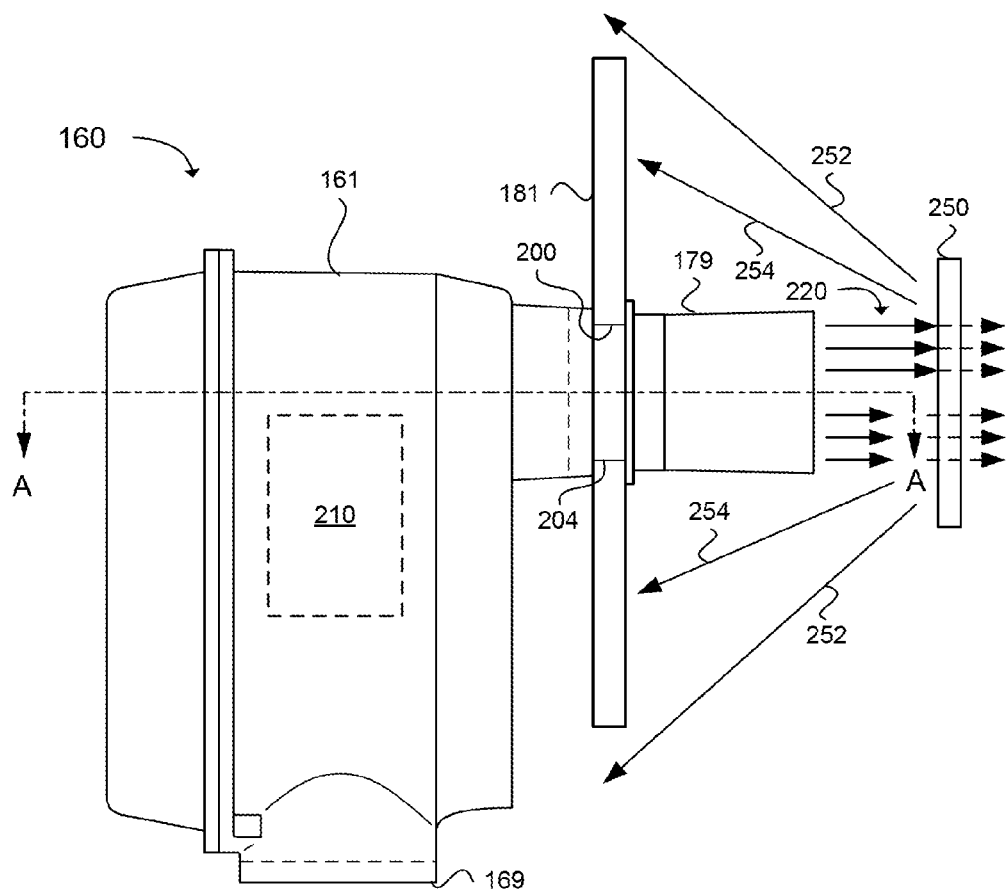
FIG. 5A is a side view of a hybrid x-ray device for mounted and portable use with a detachable radiation shield.

FIG. 5A illustrates one or more shield connectors in the form of a coupling point of the radiation shield 181 (connector 200 in FIG. 5A) and coupling point of the x-ray tube head 160 (connector 204 in FIG. 5A). In addition to the radiation shield presence identification features just described, the hybrid x-ray system 155 may include features to ensure that only a particular radiation shield is mated with or attached to the x-ray tube head 160. In one embodiment, the connector 200 and connector 204 are configured with mating features that only allow a particular radiation shield 181 (for example, a shield meeting certain manufacturer requirements) to be attached to the x-ray tube head 160. After the radiation shield 181 is attached and mated via the connectors 200 and 204, information from the shield sensor 184 can be used to confirm that the radiation shield 181 is properly in place. The information or signal from the shield sensor 184 can also be used by a processor or interlock 210 located, for example, in the x-ray tube head housing 161, to enable emission of x-ray radiation.

Figure 5B:
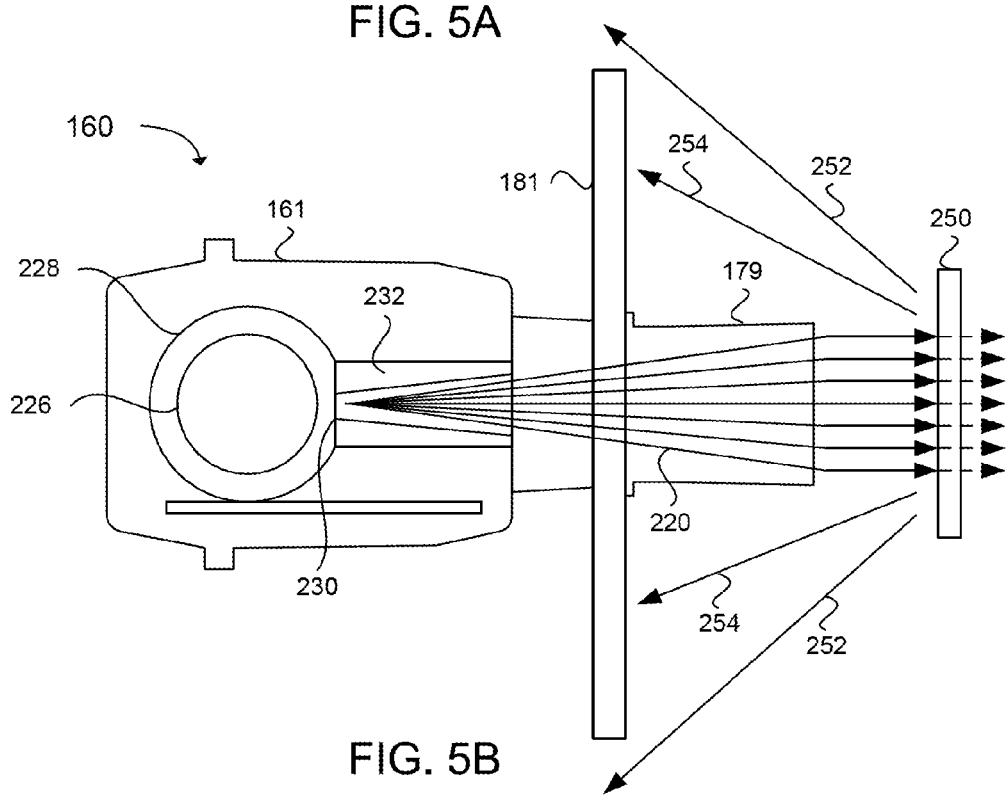
FIG. 5B is a top section view of a hybrid x-ray device for mounted and portable use with a detachable radiation shield of FIG. 5A.

FIG. 5A illustrates the x-ray tube head 160 with a radiation shield 181 from the side. FIG. 5B is a schematic, top section view along the A-A axis of FIG. 5A. Although x-rays are generally invisible, a representation of an x-ray stream 220 is illustrated to facilitate understanding of the embodiment illustrated. In the example provided, the x-ray tube head 160 includes an x-ray tube 226 that is designed to emit x-rays. The x-ray tube 226 is surrounded by a shield 228 having an opening 230. A tube shield 232 is positioned adjacent to the opening 230. The tube shield 232 generally collimates the x-ray stream 220 into a specified shape. A collimator cone 179 may be attached to the x-ray tube head 160 to further collimate the x-ray stream 220. The radiation shield 181 can be sandwiched between the x-ray tube head housing 161 and the collimator cone 179. In one example, the collimator cone 179 is coupled to the x-ray tube head 160 and/or radiation shield 181 via a threaded feature, a snap-on feature, a latched feature, or a combination of such features.

Instead of being located between the x-ray tube head 160 and the collimator cone 179, the radiation shield 181 can be coupled to the free end of the collimator cone 179. In this configuration, the collimator cone 179 can include circuitry or other features that permit sensing of the radiation shield 181.

As previously discussed, x-ray stream 220 emitted from the x-ray tube head 160 is directed to an anatomical area of interest or target area (e.g., without limitation, a patient's teeth, cheek, gums, and/or jaw), which is schematically shown as an object 250 in FIGS. 5A and 5B. A portion of the x-ray stream 220 passes through the object 250 and portion of the x-rays reflects off the object 250. In FIGS. 5A and 5B, the reflected x-rays are illustrated as scatter x-rays 252 and 254. Some of the scatter radiation is absorbed and/or reflected by the radiation shield 181, thus reducing exposure to the operator.

Figure 6:
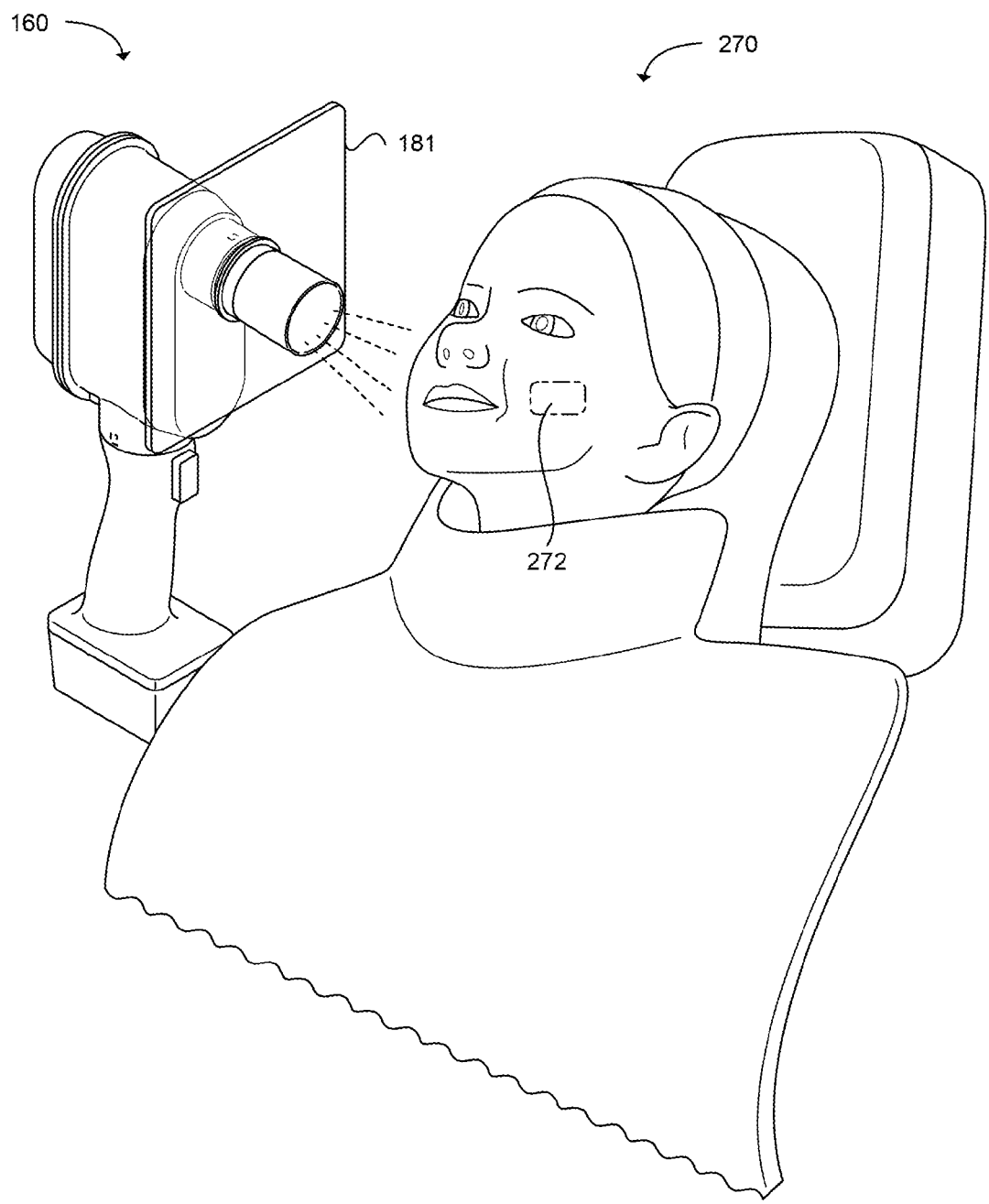
FIG. 6 is a perspective view of a hybrid x-ray device with a detachable radiation shield configured for portable use.

FIG. 6 illustrates the x-ray tube head 160 configured as a portable x-ray device, and used in x-ray imaging of a patient 270 with an x-ray sensor 272. The shield 181 is attached to the x-ray tube head 160.

Figure 7:
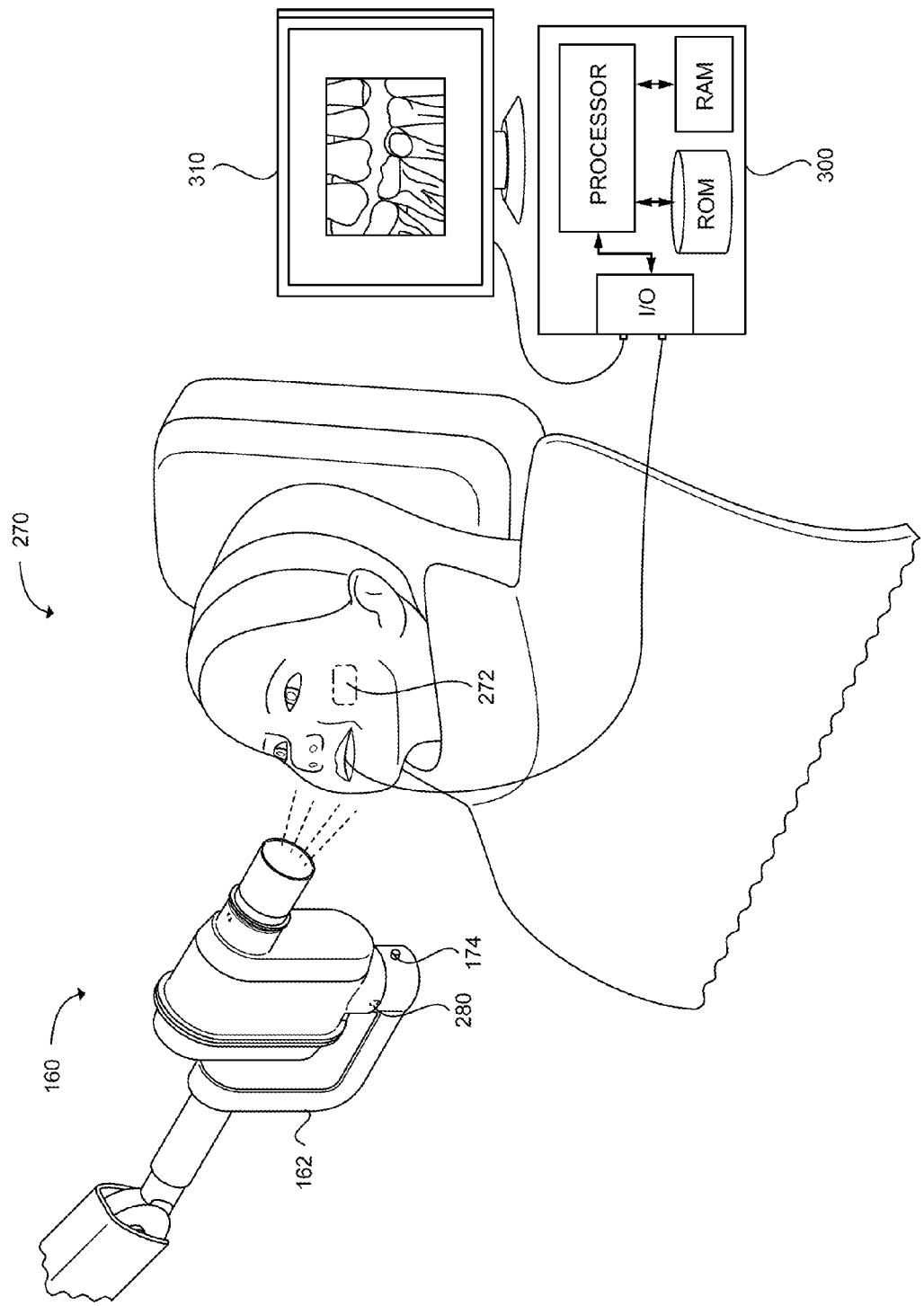
FIG. 7 is a hybrid x-ray device without a detachable radiation shield coupled to a support arm.

As best seen by reference to FIGS. 3 and 7, in another mode of operation of the hybrid x-ray system 155, the x-ray tube head 160 is connected to the support arm 162 and used in a wall-mount or fixed mode of operation. In this mode, the x-ray tube head 160 can be used without the radiation shield 181. As shown in FIG. 3, the x-ray tube head 160 is docked (or otherwise coupled) to the articulating extension arm 163. The fixed mount configuration allows the hybrid x-ray system 155 to be used with standard film/plate/digital sensor holding, alignment, and placement devices available in the market for fixed mounted x-ray systems, such as the system 50 (FIG. 1). As previously discussed, when the radiation shield 181 is not coupled to the x-ray tube head 160, the x-ray tube head 160 should preferably be coupled to the support arm 162 to help ensure that the operator is protected from x-ray exposure during x-ray imaging. In order to ensure coupling of the x-ray tube head 160 to the support arm 162, sensors, switches, or similar devices can be included in the x-ray tube head 160 and/or the support arm 162 to detect the docking state of the x-ray tube head 160.

Typically, an x-ray controller is located in the base 164 (FIG. 3), but the x-ray controller may be located in different portions of the hybrid x-ray system 155. In one configuration, the x-ray controller is located in the x-ray tube head 160. The x-ray controller board can be located in the base 164, the x-ray tube head 160, the handle 171, or a different portion of the system as long as the x-ray controller can communicate with other components of the systems, which could, for example, be achieved using wireless communications between the components.

When the x-ray tube head 160 is docked to the support arm 162, the control circuitry allows the x-ray tube head 160 to be armed for an exposure regardless of the presence or absence of the radiation shield 181.

The plug end 165 (FIG. 3) can include a power coupling to a wall power source and/or a control coupling to a remote switch, control, and/or GUI. In configurations where the same socket 169 (FIG. 3) of the x-ray tube head 160 is used to couple the x-ray tube head 160 to the handle 171 or the plug end 165 of the support arm 162, the plug end 165 may include mating features with the x-ray tube head 160 that can mechanically indicate to a switch or sensor that the x-ray tube head 160 is coupled to the plug end 165 instead of the handle 171. The x-ray tube head 160 can include a support arm sensor or support sensor 280 (FIG. 7) to detect the plug end 165, which allows the x-ray tube head 160 to arm and trigger an x-ray exposure.

The x-ray tube head 160 can operate off of DC power from a battery or wall power. Alternatively, in one configuration, the x-ray tube head 160 can operate off of DC power from a battery or AC power from wall power. In such a configuration, control components (e.g., interlock 210 or power circuitry 360) in the x-ray tube head 160 may detect the type of power used by the device and determine that the x-ray tube head 160 is coupled to a fixture connector (e.g., plug end 165) of the support arm 162 when the x-ray tube head 160 is operating off AC power. The control components may also determine that the x-ray tube head 160 is not coupled to the fixture connector of the support arm 162 (i.e., coupled to the handle 171) when the x-ray tube head 160 is operating off DC power (or not powered). Other processes and mechanisms can be used to determine when the x-ray tube head 160 is operating off of wall power or coupled to the support arm 162 and when the x-ray tube head 160 is operating off of battery power or coupled to the handle 171. A process for using a power type determination or a connector type determination to enable and/or disable the x-ray tube head 160 is described in greater detail below in relation to FIG. 10.

Typically, features (e.g., springs and pulleys) of the extension arm 163 (FIG. 3) are calibrated for the weight of the x-ray tube head 160 so the extension arm 163 can move freely without significant effort by the operator. When the x-ray tube head is detached from the extension arm, the resulting loss of load or weight may cause the links 163B and 163C to either spring up or slap against each other. In one configuration, the brake 163D is used to prevent springing up or slapping of the links when the x-ray tube head weight is removed from the extension arm 163.

In embodiments in which no brake is used, the extension arm 163 may include a lock mechanism (not shown) to prevent the detachment of the x-ray tube head 160 unless the extension arm 163 is folded in and/or locked into a specified position. Such a feature can also prevent springing up or slapping of the links 163B and 163C.

Referring back to FIG. 7, the x-ray tube head 160 is coupled to the support arm 162 in a fixed mount configuration. The patient 270 in FIG. 7 is shown with x-ray sensor 272 in her mouth. However, other kinds of x-ray receptors— e.g., film or phosphor plates—can also be used. In the illustrated example, the x-ray sensor 272 is coupled to a computer 300 that includes a processor, memory, an input/output interface, and a monitor 310. The computer may include software and otherwise be configured to process information from the sensor 272, generate an electronic x-ray image, and display the x-ray image on the monitor 310.

Figure 8A:
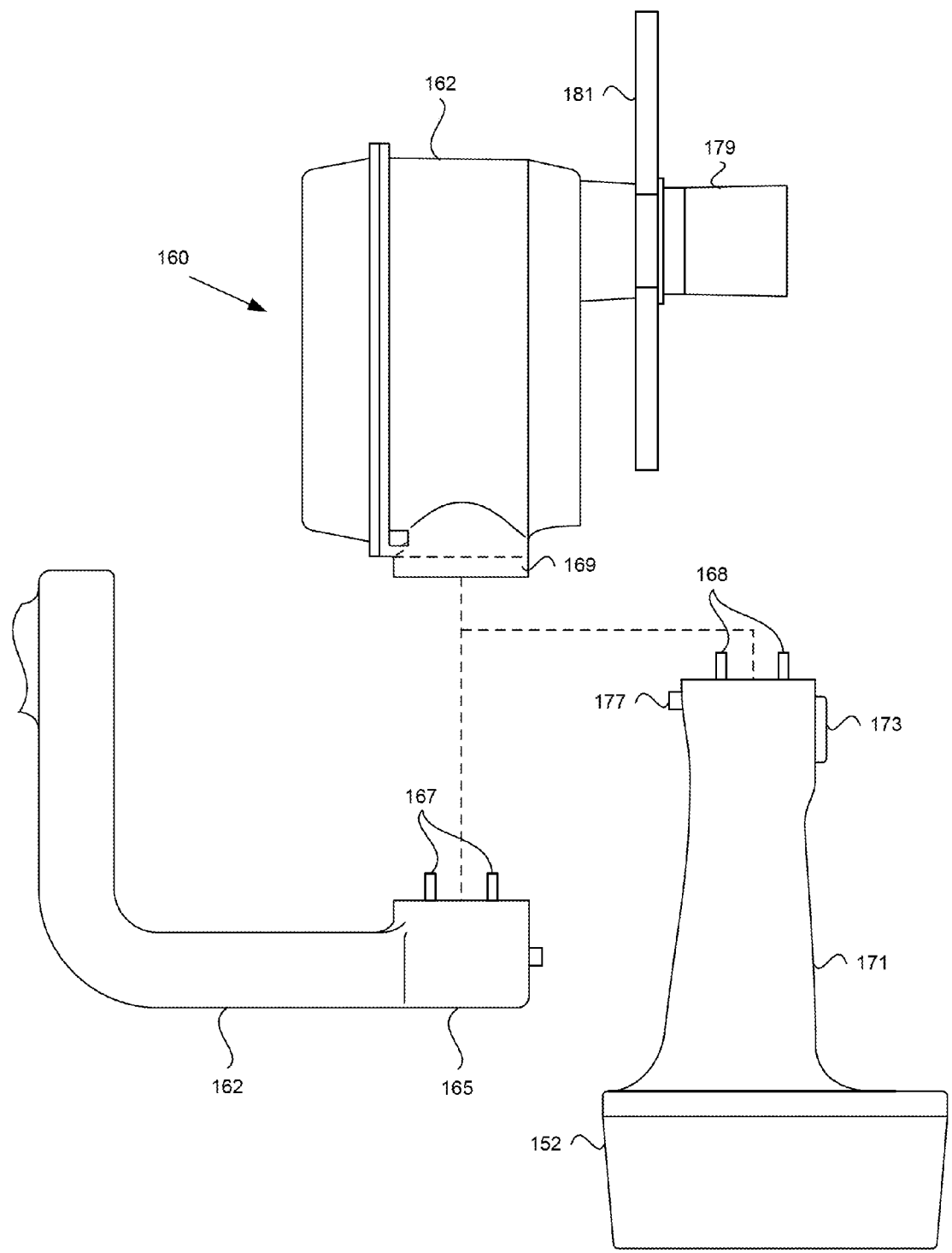
FIG. 8A is a side view of coupling points of a support arm and coupling points of a battery pack for the hybrid x-ray device.

FIG. 8A illustrates the x-ray tube head 160 of the hybrid x-ray system 155 with a connector (e.g., receptacle or socket 169) configured for a connection to the handle 171 for portable use and for a connection to the plug end 165 of a support arm 162. The handle 171 includes electrical contacts 168 to provide power from a battery 152, control signals from the trigger 173 (or other controls) to the x-ray tube head 160, and/or detect that the handle 171 is connected. The plug end 165 of the support arm 162 includes electrical contacts 167 to provide wall power, control signals from the RC (or other controls) to the x-ray tube head 160, and/or detect that the support arm 162 is connected. Alternatively or in addition, the socket 169 can be on the handle 171 or on the end 165 of the support arm 162, and the plug can be on the x-ray tube head 160.

Figure 8B:
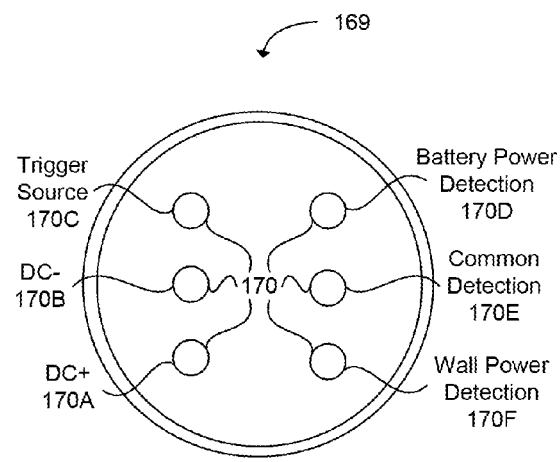

FIG. 8B illustrates a bottom view of the socket 169 (i.e., the support connector or receptacle) for an x-ray tube head 160. The connector includes six contacts 170 (e.g., electrical sockets, receptacles, or terminals), which are further categorized as power contacts, a control contact, and detection contacts. The power contacts include a positive DC (DC+) contact 170A and negative DC (DC−) contact 170B for receiving input power. The control contact includes a trigger source contact 170C used to receive a signal indicating that the user pushed a trigger button (e.g., either trigger 173 on the handle 171 in the handheld configuration, or the remote control in another room in the wall or ceiling mounted configuration), which then initiates an x-ray pulse from the x-ray tube head 160. The detection contacts include three contacts 170D-F used to determine when the x-ray tube head 160 is coupled to the support arm 162 or the handle 171 via a pattern of shorts. The detection contacts can be used alternatively or in addition to other mechanism (e.g., sensors or power type determination) for detecting when the x-ray tube head 160 is coupled to the support arm 162 or the handle 171.

Figures 8C, 8D:
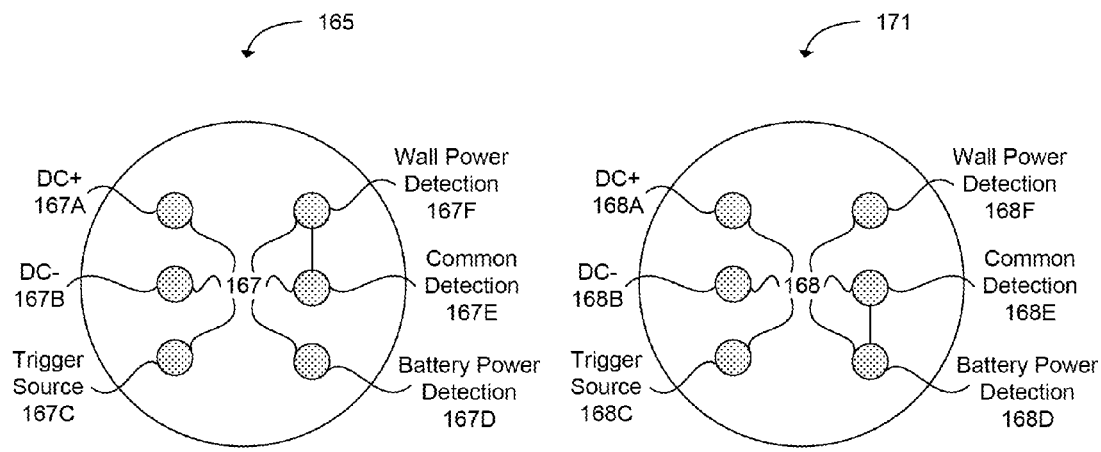

FIG. 8C illustrates a top view of the plug end 165 (i.e., the fixture connector) for the support arm 162 corresponding to the socket 169 of the x-ray tube head 160. The plug end 165 of the support arm 162 can mate to the socket 169 of the x-ray tube head 160. The six contacts 170A-F (e.g., electrical sockets or electrical receptacles) of the socket 169 of the x-ray tube head 160 have six corresponding contacts 167A-F on the plug end 165 of the support arm 162. The power contacts 167A-B provide wall power to the x-ray tube head 160. A trigger source contact 167C provides the trigger signal from the remote control in another room in the wall or ceiling mounted configuration indicating that the user pushed the trigger button. The plug end 165 includes a wall power detection contact 167F, a common detection contact 167E, and an optional battery power detection contact 167D. The wall power detection contact 167F and the common detection contact 167E are coupled or shorted together, which is illustrated schematically in FIG. 8C. As discussed in greater detail below, when the x-ray tube head 160 is coupled to the support arm 162, the processor 354 and/or interlock 210 of the x-ray tube head 160 can detect that x-ray device is operating in the wall mounted configuration.

FIG. 8D illustrates a top view of the handle 171. As noted above, the handle 171 can mate to the socket 169 of the x-ray tube head 160. FIG. 8D illustrates six contacts 168A-F (e.g., electrical pins) of the handle 171. The contacts 168A-F correspond to the contacts 170A-F of the socket 169. The power contacts 168A-B provide battery power to the x-ray tube head 160. A trigger source contact 168C provides the trigger signal from the trigger 173 on the handle 171 in the handheld configuration indicating that the user pushed the trigger button. The handle 171 includes a battery power detection contact 168D, a common detection contact 168E, and an optional wall power detection contact 168F. As illustrated schematically in FIG. 8D, the battery power detection contact 167D and the common detection contact 167E are coupled or shorted together. When the x-ray tube head 160 is coupled to the handle 171, the processor 354 and/or interlock 210 of the x-ray tube head 160 can detect that x-ray device is operating in the handheld configuration.

FIGS. 8A-8D illustrate the x-ray tube head 160 with a socket 169 (i.e., receptacle or female connector) that includes electrical sockets (i.e., contacts 170) to receive the pins (i.e., contacts 167) of the corresponding plug end 165 of the support arm 162 or the pins (i.e., contacts 168) of the corresponding connection end of the handle 171. In another configuration, the x-ray tube head can include a plug with electrical pins (i.e., male components) that couple to a socket, receptacle, or female connector that includes electrical sockets (i.e., female components) of the fixture connector of the support arm 162 or the connection end of the handle 171. The x-ray tube head 160, support arm 162, and handle 171 can have other arrangements of corresponding male and female components for the connectors and the contacts. In FIGS. 8B-8D, the contacts 167, 168, and 170 are shown having a round shape. In other embodiments, the contacts can be a different shape (e.g., rectangular). FIGS. 8B-8D illustrates the contacts 167, 168, 170 as individual pins in a specified pattern (i.e., two columns or three rows). In another configuration, the contacts can be arranged in other patterns. In addition, the contacts can take a form that is different from the form illustrated. For example, the contacts could be in the form of flat contacts rather than pin and socket pairs. The contacts can also have a form similar to the form used for Universal Serial Bus (USB) connectors.

FIGS. 8E-8G illustrate an optional configuration of the socket 169, plug end 165, and connection end of the handle 171 shown in FIG. 8B-8D. The interfaces in FIGS. 8E-8G include an additional serial line 170G, 167G, and 168G, respectively. A socket 169B of the x-ray tube head 160 includes electrical sockets (i.e., contacts 170) to receive the pins (i.e., contacts 167) of the corresponding plug end 165B of the support arm 162 or the pins (i.e., contacts 168) of the corresponding connection end of the handle 171B. The socket 169B includes the contacts 170 of socket 169 (FIG. 8B) along with an optional serial line 170G contact. The plug end 165B of the support arm 162 includes the pins of socket 167 (FIG. 8C) along with an optional serial line 167G pin. The connection end of the handle 171B includes the pins of the connection end of the handle 171 (FIG. 8D) along with an optional serial line 168G contact.

The serial line 170G provides a connection between an x-ray source (e.g., 350 of FIG. 9) and the socket 169B. The connection can be used to indicate whether the x-ray tube head 160 is connected to the handle 171B or the plug end 165B of the wall or ceiling mount. In addition or alternatively, the serial line 170G is used to transmit x-ray settings (e.g., kV, milliamps, pulse time, etc.) to the x-ray source 350 (FIG. 9), interlock 210, and/or processor 354 (FIG. 9) of the x-ray tube head 160. The base 60 (e.g., a wall or ceiling mount unit) for the extension arms 52, the handle 171, and/or the x-ray tube head 160 can optionally contain communication circuitry for sending and receiving data between the x-ray tube head 160 and the base 60 or handle 171. The communication circuitry can use a serial protocol (e.g., RS-232, CAN, or Ethernet) over the serial line or a parallel protocol using additional pins and lines.

As noted, the communication circuitry can use a Controller Area Network (CAN) protocol. The CAN (or CAN bus) is a vehicle bus standard designed to allow microcontrollers and devices to communicate with each other in applications without a host computer. The CAN, for example, can provide communication on single wire, such as the serial line 170G, 167G, and 168G (shown in FIGS. 8E-8G), or on dual wires. The transmission speed of the communication link can range from around 10 kilobits per second (kbps) to 2 Megabits per second (Mbps). The communication circuitry may also operate using another physical layer protocol or configuration.

The data transmitted by the communication circuitry over the communication link (e.g., the serial line) can include, for example, setting information and/or an indication of which mount (e.g., handle 171 or plug end 165) is connected. The setting information or parameters can be further categorized as technique factors and work flow improvement settings. For example, technique factors can include tube voltage (e.g., units in kilovolts (kV)), tube current (e.g., units in milliamperes (mA)), and exposure time (e.g., units in seconds or s). In addition to the technique factors, work flow improvement settings can also be transmitted over the communication link and/or be displayed on the tube head for an improved work flow when using the hybrid x-ray device. The work flow improvement settings can include an anatomy (e.g., a tooth, which can be displayed as an image of a tooth), collimator selection (e.g., C1, C2, C3, C4, C5, and C6), selected imaging media (e.g., film, phosphor plate, or digital sensor), and dose (e.g., indicated by dose area product mGy·cm$^2$).

The setting information can be sent as signals by the communication link from the remote control to the control circuitry (e.g., x-ray source, actuator, interlock, processor, and/or power circuitry) inside the x-ray tube head 160. In an optional embodiment (not shown), the x-ray tube head can include a display and/or control keys (e.g., touch screen, keypad, selection keys, pointer device, and input devices). The display and keys on the tube head can allow for setting of the same parameters on the x-ray tube head as can be set by the remote control. As a result, the communication link with remote control may not be needed for the x-ray tube head to function (e.g., portable mode). However, the communication link with remote control can provide for optional way to configure the hybrid x-ray for use with the remote control.

FIGS. 8B-8D illustrates six contacts 167, 168, 170. FIGS. 8E-8G illustrates seven contacts 167, 168, 170. In another configuration, as previously discussed, additional contacts or fewer contacts may be used for the power contacts, control contacts, and/or detection contacts. In another embodiment, the contacts may provide a dual purpose (e.g., the common detection contact may also be used as a control contact or a power contact).

Figure 9:
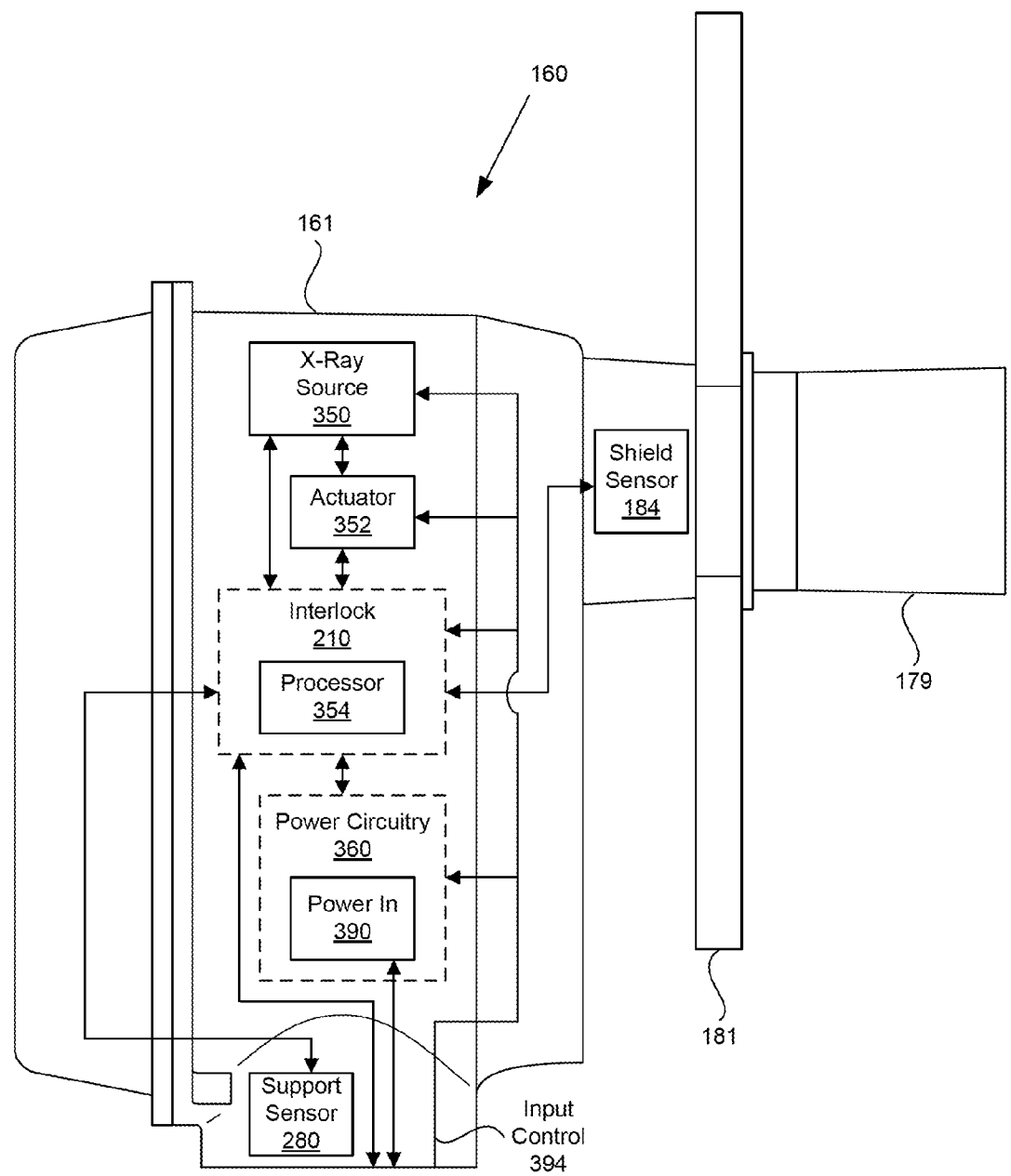
FIG. 9 is a schematic view of a hybrid x-ray device for mounted and portable use with a detachable radiation shield.

FIG. 9 schematically illustrates components of the x-ray tube head 160. The x-ray tube head 160 may include an x-ray source 350 (such as the x-ray tube 226), an actuator 352, and the interlock 210. In the embodiment shown, the interlock 210 includes a processor 354. The x-ray tube head 160 also includes power circuitry 360, the support sensor 280, and/or the shield sensor 184. The x-ray source is turned on or activated by a signal from the actuator 352 which receives a signal from the trigger source contact 170C. The power circuitry 360 includes a power input 390 and an input control 394. The power input 390 can either accept wall power or battery power from the power contacts 170A-B. The input control 394 can be coupled to the power circuitry 360, the interlock 210 and/or the processor 354, the actuator 352, the x-ray source 350, the control contact 170C, and/or the detection contacts 170D-F. Components of the x-ray tube head 160 are in communication with each other via wired connection, optical coupling, or wireless communication. Although FIG. 9 illustrates various components within the x-ray tube head 160, some of these components may be located external to the x-ray tube head 160 (e.g., in the handle 171, or in the support arm 162, and/or fixed components such as the base 164). For example, the actuator 352 may be located within the x-ray tube head 160 or be located external to the x-ray tube head 160, such as within a trigger 173 or the RC (FIG. 3).

In one configuration, the interlock 210 is used to disable the actuator 352 or a remote actuator (e.g., the RC) from powering or activating the x-ray source 350 under specified conditions, such as the x-ray tube head 160 being detached from the support arm and the radiation shield 181 being detached.

In another configuration, the interlock 210 interfaces directly with the x-ray source 350 and enables the operation and/or powering of the x-ray source when specified conditions are satisfied, such as the x-ray tube head being attached to the support arm 162, or a shield sensor 184 sensing that the radiation shield 181 is attached to the x-ray tube head 160.

Optionally, the processor 354 can be configured to perform only the functions of the interlock 210. However, the processor 354 can also be configured to perform the interlock functions along with other functions related to the hybrid x-ray system 155. The interlock 210 interfaces with a sensing element (e.g., support sensor 280 and/or power circuitry 360) that determines if the x-ray tube head 160 is coupled to the support arm (or operating off wall power). The support sensor 280 indicates when the x-ray tube head 160 via the socket 169 or other support connector is connected to the support arm 162 (instead of the handle 171).

In configurations where the support connector of the x-ray tube head 160 is configured to be connected to both the support arm assembly and the handle, as illustrated in FIGS. 3-9, the support sensor 280 can be used to distinguish between the coupling of the support arm 162 and handle 171 by only detecting the coupling of the support arm 162 as a configuration that enables the interlock 210 to enable the x-ray source 350 if the shield 181 is not present.

Alternatively or in addition, the processor 354 can be used to detect the short between the wall power detection contact 167F and the common detection contact 167E indicating that the x-ray tube head 160 is coupled to the support arm 162. The processor 354 also detects the short between the battery power detection contact 167D and the common detection contact 167E indicating that the x-ray tube head 160 is coupled to the handle 171.

In configurations where the wall power is AC power, the power circuitry 360 may be used to determine or detect when the x-ray tube head 160 is coupled to the support arm 162 based on an input power determination. Because the support arm 162 provides wall power to the x-ray tube head 160, AC power provided via the power input 390 of the power circuitry 360 indirectly indicates that the x-ray tube head 160 is coupled to the support arm 162 via the socket 169. Based on the detected input power being AC input power, the power circuitry 360 sends a signal to the interlock 210 indicating AC power is detected (or DC power is not detected). Similarly, because the handle 171 provides battery power to the x-ray tube head 160, DC power provided via the DC power input 392 of the power circuitry 360 indirectly indicates that the x-ray tube head 160 is coupled to the handle 171 and not coupled to the support arm 162. Based on the detected input power being DC input power, the power circuitry 360 sends a signal to the interlock 210 indicating DC power is detected (or AC power is not detected). As such, the hybrid x-ray device can be configured to selectively receive power from the battery and the wall power source.

The power circuitry 360 can also include features (e.g., inverter and transformer) to convert between AC and/or DC power and provides the converted voltage and/or power levels for components of the x-ray tube head 160. The interlock 210 also interfaces with another sensing element (e.g., shield sensor 184) that determines if the radiation shield 181 is coupled to the x-ray tube head 160.

Figure 10:
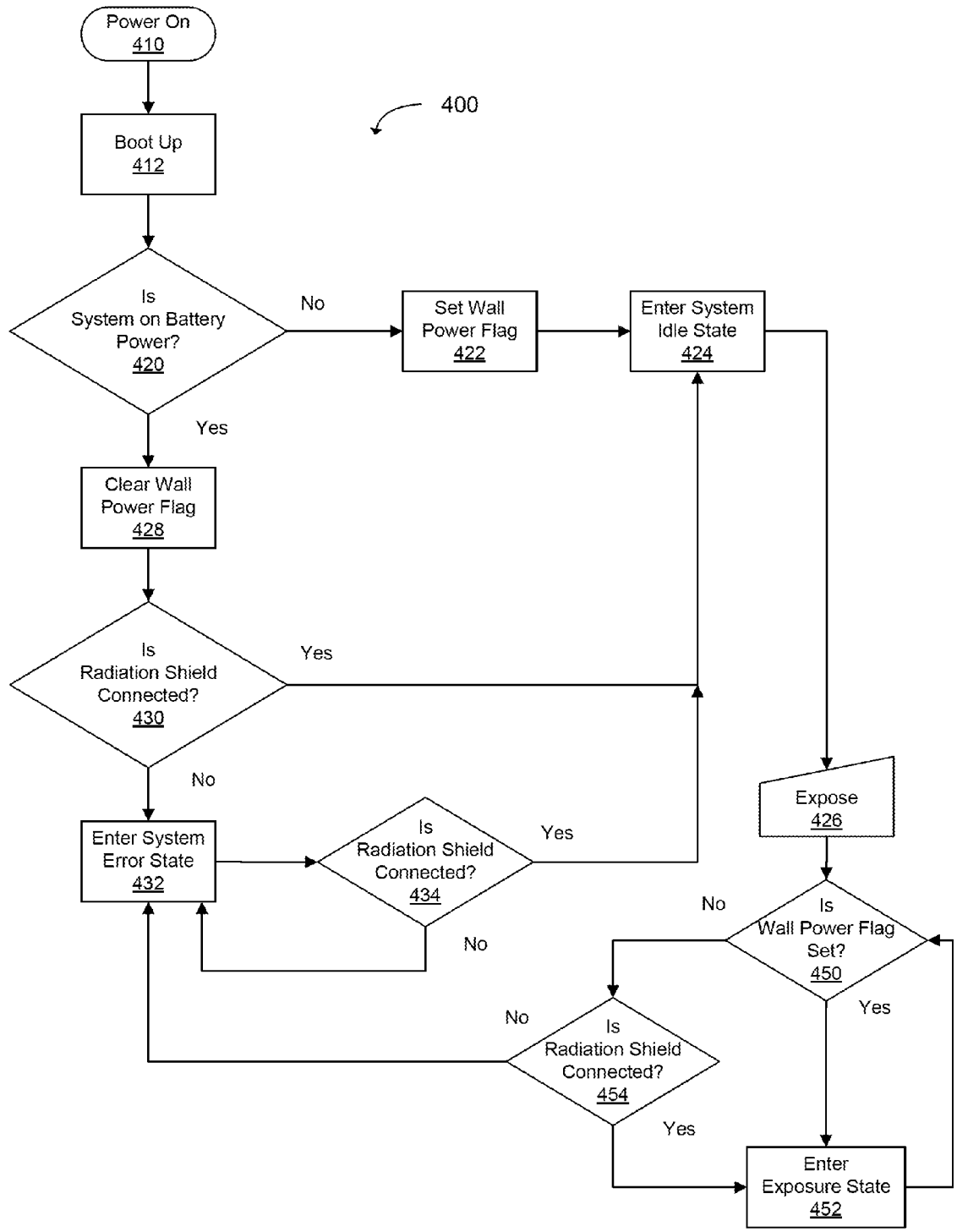
FIG. 10 is a flowchart of an exemplary process for controlling a hybrid x-ray device.

FIG. 10 illustrates a flowchart of an exemplary process 400 for disabling the operation of the x-ray source 350 until specified conditions are met—e.g., an wall power flag being set (i.e., a support connector coupled condition) and/or a radiation shield 181 being connected (i.e., a shield connector coupled condition). In one example, the process 400 of FIG. 10 is implemented using the components of FIG. 9. The process 400 starts with the x-ray tube head 160 being powered on (block 410). After power is provided, the processor 354 begins a boot up process to initialize itself (block 412). Using the power circuitry 360, the processor 354 determines if the x-ray tube head 160 operating on battery power (decision block 420). If the x-ray tube head 160 is not operating on battery power, then a wall power flag is set (block 422) and the x-ray tube head 160 enters a system idle state (block 424). In the system idle state, the processor 354 waits for the x-ray source to be triggered for an x-ray exposure (block 426). If the x-ray tube head 160 is operating on battery power, then the wall power flag is cleared (block 428).

Then the processor 354 determines if the radiation shield 181 is connected to the x-ray tube head 160 (decision block 430). If the radiation shield 181 is connected, the x-ray tube head 160 enters the system idle state (block 424). If the radiation shield 181 is not connected, the processor 354 enters a system error state (block 432). The x-ray tube head 160 remains the system error state until the radiation shield 181 is connected. Once the radiation shield 181 is connected, the x-ray tube head 160 enters the system idle state (block 424).

After an image process or x-ray exposure (block 426), the processor 354 determines if the wall power flag is still set (block 450). If the wall power flag is still set, then the x-ray tube head 160 enters an exposure state (block 452). The exposure state is similar to the system idle state, where the processor 354 waits for the x-ray source 350 to be triggered for an x-ray exposure. If the wall power flag is not set, the processor 354 determines if the radiation shield 181 is connected (block 454) to the x-ray tube head 160. If the radiation shield 181 is connected, the processor 354 enters the exposure state (block 452). If the radiation shield 181 is not connected, the processor 354 enters a system error state (block 432). In this way, the processor provides an interlock against accidental x-ray emissions unless the radiation shield 181 is connected and/or wall power is applied. Other methods providing similar functionality, such as using a battery power flag instead of a wall power flag, may also be used.

Figure 11:
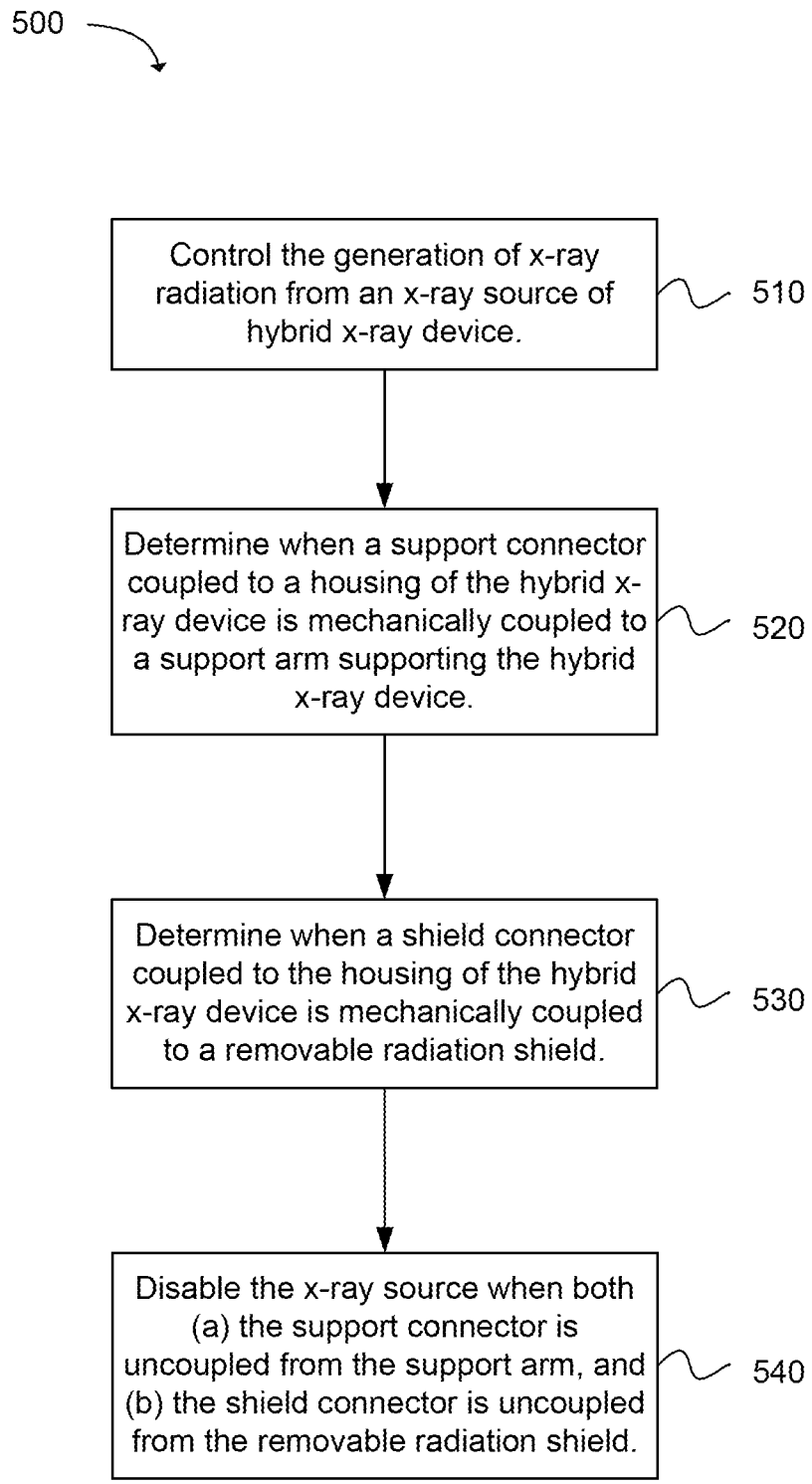
FIG. 11 is a flowchart of an exemplary process for disabling generation of x-ray radiation from an x-ray source in a hybrid x-ray device.

Another exemplary method, method 500, is illustrated in FIG. 11. The method 500 includes a process for disabling generation of x-ray radiation from an x-ray source in a hybrid x-ray device. The method begins control (for example, by reading input or settings provided by a user) of the generation of x-ray radiation from an x-ray source of hybrid x-ray device, as in block 510. The second step includes a determination of when a support connector coupled to a housing of the hybrid x-ray device is mechanically coupled to a support arm supporting the hybrid x-ray device, as in block 520. The next step includes a determination of when a shield connector coupled to the housing of the hybrid x-ray device is mechanically coupled to a detachable radiation shield, as in block 530. The x-ray source is disabled when both (a) the support connector is uncoupled from the support arm, and (b) the shield connector is uncoupled from the detachable radiation shield, as in block 540.

The x-ray source is enabled to emit x-rays when (a) the support connector is coupled to the support arm, and/or (b) the shield connector is coupled to the removable radiation shield. The x-ray source to emit x-rays.

The support sensor senses when the support connector of the hybrid x-ray device is mechanically coupled to the support arm. Alternatively, it is assumed that the support connector of the hybrid x-ray system is mechanically coupled to the support arm when wall power is applied. The shield sensor senses when the shield connector of the x-ray tube head is mechanically coupled to the detachable radiation shield.

While the forgoing examples are illustrative of the principles of the present invention in one or more particular applications, it will be apparent to those of ordinary skill in the art that numerous modifications in form, usage and details of implementation can be made without departing from the principles and concepts of the invention. Accordingly, it is not intended that the invention be limited, except as by the claims set forth below.

What is claimed is:

1. A hybrid x-ray system comprising:
   an x-ray device for mounted and portable use and including,
      a housing,
      an x-ray source coupled to the housing and configured to generate x-ray radiation,
      a support connector coupled to the housing and including a mechanical connector; and
      power circuitry connected to the x-ray device and configured to selectively connect a battery to the x-ray device and a power source to the x-ray device based on whether the support connector is coupled to a support arm or coupled to a handle.

2. The hybrid x-ray system of claim 1, wherein the x-ray device includes power circuitry having a power input and an input control and that is configured to convert between AC power and DC power.

3. The hybrid x-ray system of claim 1, wherein the support arm includes power circuitry configured to convert between AC power and DC power.

4. The hybrid x-ray system of claim 1, wherein the support arm includes a plug end that includes one or more electrical contacts for providing electrical power.

5. The hybrid x-ray system of claim 4, further comprising a support sensor coupled to the support connector or the support arm and configured to detect when the support arm is coupled to the support connector.

6. The hybrid x-ray system of claim 1, further comprising an interlock coupled to the x-ray source and configured to disable activation of the x-ray source.

7. The hybrid x-ray system of claim 6, wherein the interlock is configured to determine a support connector coupled condition when the support connector is coupled to the support arm.

8. A hybrid x-ray system comprising:
   an x-ray device for mounted and portable use and including,
      a housing,
      an x-ray source coupled to the housing and configured to generate x-ray radiation, and
      a support connector coupled to the housing and configured to mechanically couple to a support arm;

a battery configured to provide power to the x-ray device; and the support arm having a plug end that includes one or more electrical contacts for providing electrical power, wherein the x-ray device is configured to selectively receive power from the battery and from the electrical contacts of the support arm.

9. The hybrid x-ray system of claim 8, wherein the x-ray device includes power circuitry having a power input and an input control and that is configured to convert between AC power and DC power.

10. The hybrid x-ray system of claim 8, wherein the support arm includes power circuitry configured to convert between AC power and DC power.

11. The hybrid x-ray system of claim 8, further comprising a support sensor coupled to the support connector or the support arm and configured to detect when the support arm is coupled to the support connector.

12. The hybrid x-ray system of claim 11, wherein power is provided from the electrical contacts of the support arm when the support arm is coupled to the support connector.

13. The hybrid x-ray system of claim 11, wherein power is provided from the battery when the support arm is not coupled to the support connector.

14. The hybrid x-ray system of claim 8, further comprising an interlock coupled to the x-ray source and configured to disable activation of the x-ray source.

15. The hybrid x-ray system of claim 14, wherein the interlock is configured to determine a support connector coupled condition when the support connector is coupled to the support arm.

\* \* \* \* \*